(12) United States Patent
Norton et al.

(10) Patent No.: US 11,471,153 B2
(45) Date of Patent: Oct. 18, 2022

(54) SUTURE CAPTURE DEVICE AND METHOD OF CAPTURING A SUTURE

(71) Applicant: Biomet Manufacturing, LLC, Warsaw, IN (US)

(72) Inventors: Daniel R. Norton, Warsaw, IN (US); Gregory J. Denham, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 482 days.

(21) Appl. No.: 15/418,129

(22) Filed: Jan. 27, 2017

(65) Prior Publication Data
US 2017/0215876 A1 Aug. 3, 2017

Related U.S. Application Data

(60) Provisional application No. 62/289,405, filed on Feb. 1, 2016.

(51) Int. Cl.
*A61B 17/04* (2006.01)
*A61B 17/00* (2006.01)

(52) U.S. Cl.
CPC ...... *A61B 17/0485* (2013.01); *A61B 17/0482* (2013.01); *A61B 2017/00349* (2013.01)

(58) Field of Classification Search
CPC .................. A61B 17/0485; A61B 2017/00349
See application file for complete search history.

(56) References Cited

U.S. PATENT DOCUMENTS

| | | | | | |
|---|---|---|---|---|---|
| 5,364,365 | A | * | 11/1994 | Wortrich | A61B 17/3496 604/158 |
| 5,643,292 | A | * | 7/1997 | Hart | A61B 17/0469 112/169 |
| 5,817,111 | A | * | 10/1998 | Riza | A61B 17/0483 606/148 |

(Continued)

OTHER PUBLICATIONS

"Arthroscopic Rotator Cuff Repair—Medium Supraspinatus Tear [Video]", Bone and Joint Clinic of Houston, [Online]. Retrieved from the Internet: <URL: https://youtu.be/Vwkq-RnrwpU>, (Uploaded: Nov. 24, 2007), 3:06 Minutes.

(Continued)

*Primary Examiner* — Elizabeth Houston
*Assistant Examiner* — Lindsey Bachman
(74) *Attorney, Agent, or Firm* — Schwegman Lundberg & Woessner, P.A.

(57) ABSTRACT

Devices used to capture sutures are described. More particularly, suture capture devices described herein include an elongate cannulated tool having a first end with a sharpened point configured to pierce tissue, and an elongate hook member positioned within a hollowed center region of the elongate cannulated tool that has a hook on a first end of the elongate hook member proximate the sharpened point of the elongate cannulated tool. The elongate hook member is capable of advancing and retracting within the elongate cannulated tool. The devices further include a handle positioned on a second end of the elongate cannulated tool that includes a trigger that advances the hook into or out of the first end of the elongate cannulated tool when pushed in a first or second direction. Methods of capturing a suture using such a device are also described.

6 Claims, 10 Drawing Sheets

(56) References Cited

U.S. PATENT DOCUMENTS

| | | | |
|---|---|---|---|
| 2014/0012292 A1* | 1/2014 | Stewart | A61B 17/0485 606/148 |
| 2015/0018940 A1* | 1/2015 | Quill | A61F 2/2442 623/2.11 |
| 2015/0025550 A1* | 1/2015 | Heneveld | A61B 17/0469 606/144 |

OTHER PUBLICATIONS

"Brochure: IDEAL™ Suture Shuttle with CHIA", Ideal Suture Management Family, [Online]. Retrieved from the Internet: <URL: http://www.smogshoulder.com/images/Ideal__Shuttle__Brochure.pdf>, 2 pgs.

"Pivot NanoPass Reach Suture Mangers: Reference Guide", Stryker Sports Medicine, (Accessed: Nov. 17, 2015), 2 pgs.

"Pivot NanoPass Suture Mangement System: Data Sheet", Stryker Sports Medical, (Accessed: Nov. 17, 2015), 2 pgs.

\* cited by examiner

SUTURE CAPTURE DEVICE AND METHOD OF CAPTURING A SUTURE

CROSS-REFERENCE TO RELATED APPLICATIONS

The present application claims the benefit of the filing date of U.S. Provisional Application Ser. No. 62/289,405, filed Feb. 1, 2016, the disclosure of which is incorporated by reference herein in its entirety.

BACKGROUND

Suturing soft tissue is common in a number of surgical procedures. In many cases, the soft tissue must be punctured, and a tool must be used to push or pull the suture through the tissue. Where a suture is being accessed at a location difficult to access or view during the surgery, current surgical tools may require the creation of multiple holes in a given piece of tissue until a tool is placed into contact with the suture and capable of grasping and routing the suture to a desired location.

OVERVIEW

The present inventors have recognized, among other things, that a problem to be solved can include current difficulties in capturing a suture after a puncture in the soft tissue through which the suture is to be routed has been created. The present subject matter can help provide a solution to this problem, such as by providing a suture capture device that allows for a greater degree of freedom for suture opening placement by providing a device that can be rotated to contact a suture that is not immediately proximate the hole in the tissue, and capture the suture via an appropriate mechanism.

In one example, the present description provides a suture capture device that includes an elongate cannulated tool, an elongate hook member and a handle positioned on an end of the elongate tool. The elongate cannulated tool includes a first end that has a sharpened point configured to pierce tissue. The elongate hook member is positioned within a hollowed center region of the elongate cannulated tool and includes a hook on a first end of the elongate hook member proximate the sharpened point of the elongate cannulated tool. The elongate hook member is capable of advancing and retracting within the elongate cannulated tool. The handle is positioned on a second end of the elongate cannulated tool opposite the first end and includes a trigger that advances the hook out of the first end of the elongate cannulated tool when moved in a first direction and retracts the hook into the hollowed portion of the elongate cannulated tool when moved in a second direction opposite the first direction.

In another example, the present description provides a method of capturing a suture. The method includes inserting a first end of an elongate cannulated tool into an incision proximate a suture; advancing an elongate hook member through a hollowed center region of the elongate cannulated tool, a hook of the elongate hook member advancing out a first end of the elongate cannulated tool; engaging the hook with the suture; locking the suture into position with respect to the hook; and moving the suture to a desired position by moving the elongate cannulated tool.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
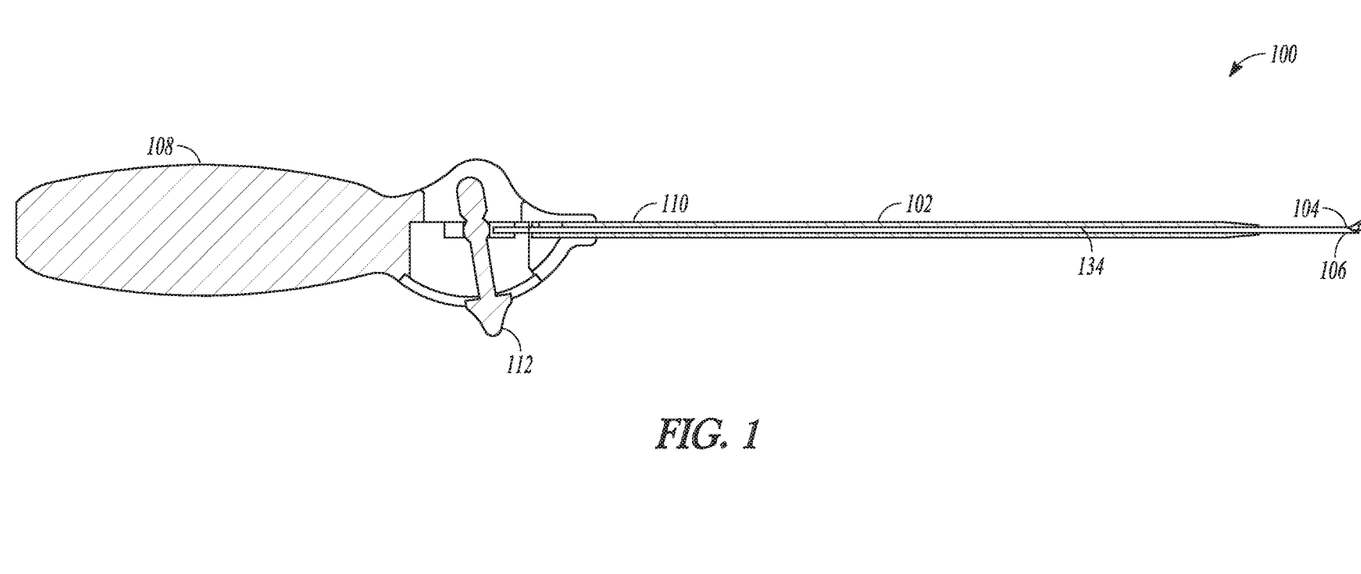
FIG. 1 provides a side view of an exemplary suture capture device according to the present description.

FIG. 1 provides a side view of a suture capture device 100 according to the present description. The suture capture device 100 described herein may be particularly useful as a tool used to aid in suturing during hip and shoulder arthroscopic procedures, though other uses are also contemplated. The suture capture device 100 can include an elongate cannulated tool 102 having a hollowed center region 134. In one example, the elongate cannulated tool 102 can be made of a high strength, durable material, such as surgical grade appropriate metal. For example, the elongate cannulated tool 102 can be made of stainless steel or titanium. A first end 104 of the elongate cannulated tool can include a sharpened point 106 that is capable of piercing tissue. The elongate cannulated tool 102 can further include a handle 108 that can be positioned on a second end 110 of the elongate cannulated tool 102. The handle 108 can include a trigger 112 for advancing and retracting a hook member. The trigger can include a traditional trigger, as illustrated, or potentially another mechanism, such as, e.g., a thumb wheel that advances or retracts the trigger by turning. The hook member of the suture capture device can be better understood by reference to FIGS. 2A and 2B.

Figure 2A:
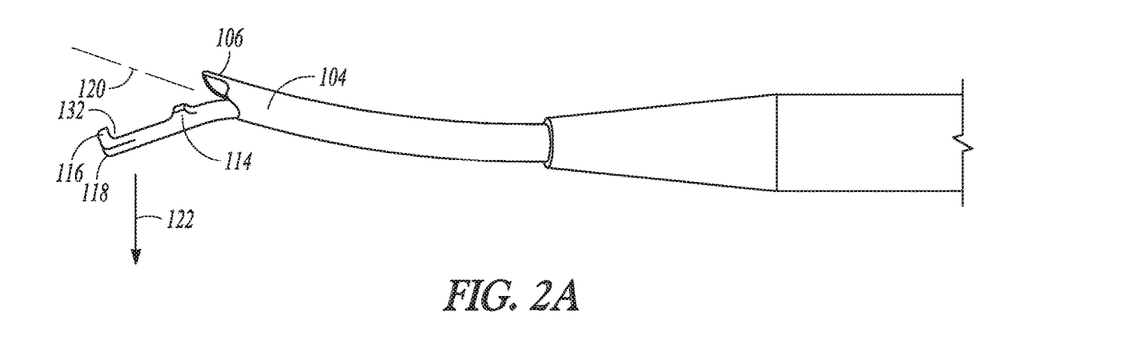
FIG. 2A provides a side view of a first end of an exemplary cannulated instrument in a first configuration according to the present description.
Figure 2B:
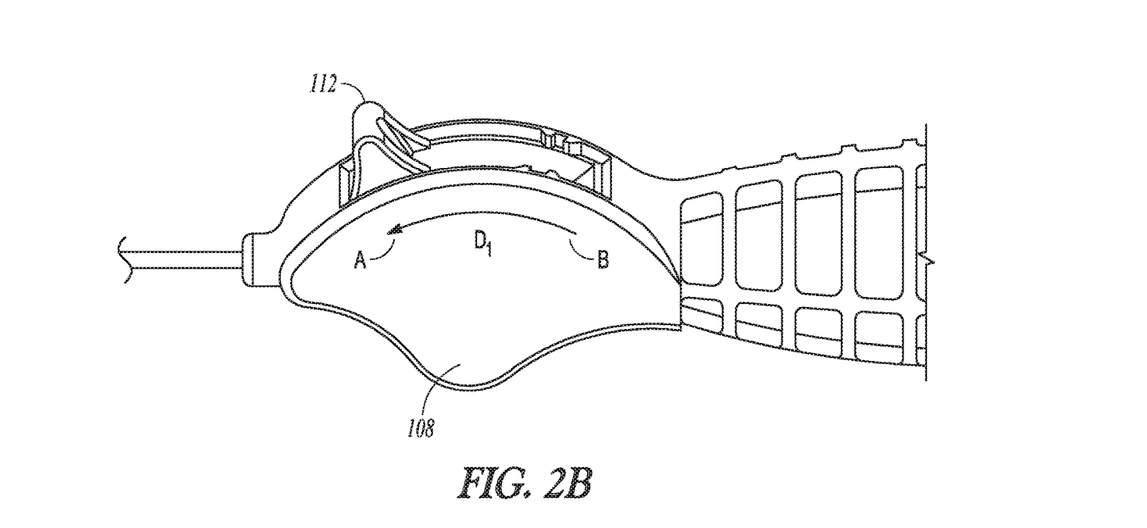
FIG. 2B provides a perspective view of a handle of an exemplary suture capture device in a first configuration according to the present description.
Figure 3A:
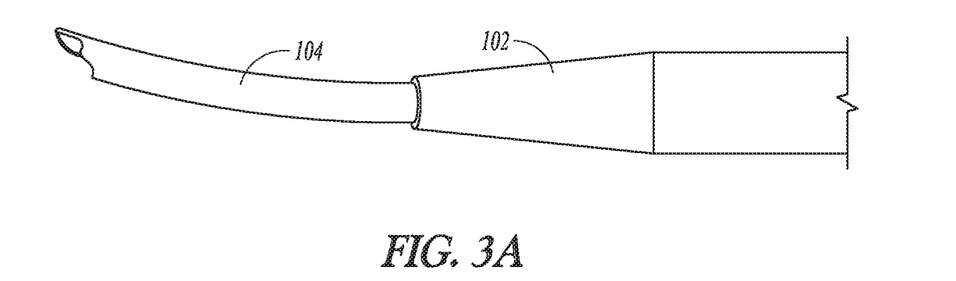
FIG. 3A provides a side view of a first end of an exemplary cannulated instrument in a second configuration according to the present description.
Figure 3B:
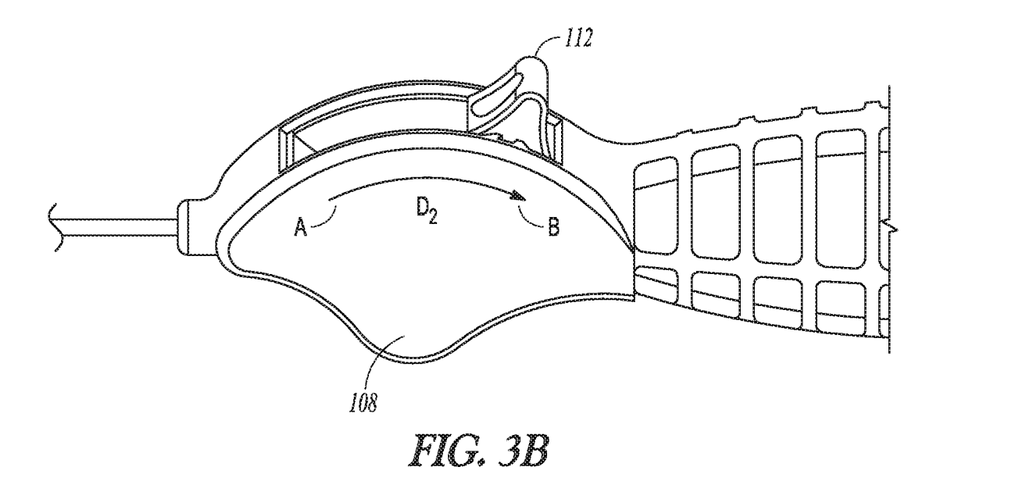
FIG. 3B provides a perspective view of a handle of an exemplary suture capture device in a second configuration according to the present description.

FIG. 2A provides a detailed view of the first end 104 of the elongate cannulated tool 102 in one configuration, and FIG. 2B provides a detailed view of the handle 108 in the same configuration. As shown in FIG. 2A, the suture capture device can further include an elongate hook member 114 that is positioned within the hollowed center region 134 of the elongate cannulated tool 102. The elongate hook member 114 can preferably be made of a material that is durable but offers greater flexibility than the elongate cannulated tool 102. For example, the elongate hook member can be made partially or entirely of nitinol. The elongate hook member 114 can include a hook 116 that can be positioned on a first end 118 of the elongate hook member 114. The hook 116 can include a recess 132 that is of sufficient depth to accommodate at least one of a #1 or #2 suture. The elongate hook member 114 can be capable of being advanced and retracted within the elongate cannulated tool 102. As further shown in FIG. 2B, when the trigger 112 on handle 108 is moved in a first direction $D_1$ towards fully advanced position A, the hook 116 can be advanced out of the first end 204 of the elongate cannulated tool 102. When the hook 116 is advanced, a portion of the elongate hook member 114 that is proximate the hook 116 (e.g. the first end 118) can curve in a direction 122 that is away from an axis 120 of the sharpened point 106. As further illustrated in FIGS. 3A and 3B, when the trigger 112 is moved in a second direction $D_2$, opposite the first direction, $D_1$, the hook 116 (hidden in FIG. 3A) can be retracted into the hollowed portion of the elongate cannulated tool 102.

Figure 4A:
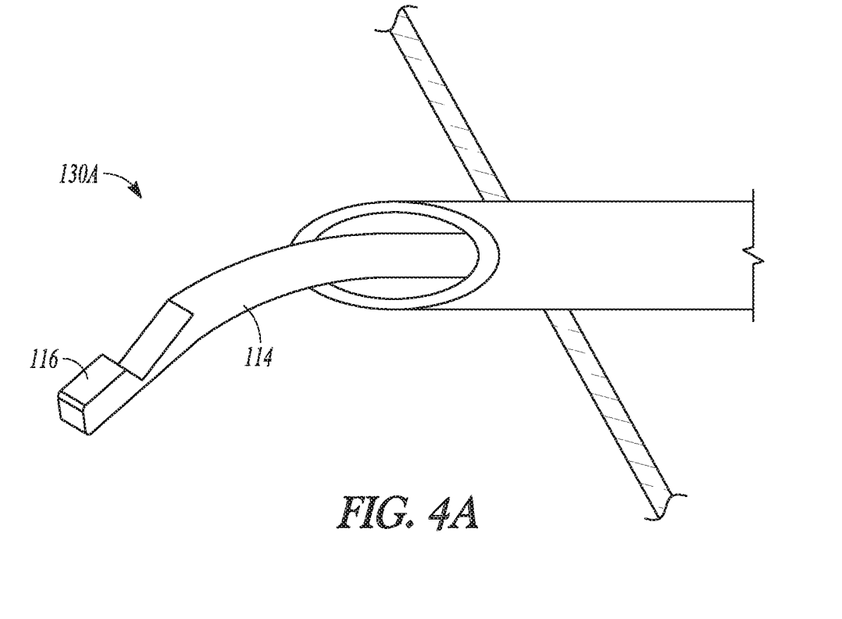
FIG. 4A provides a view of the hook of an exemplary suture capture device in a first rotatable position according to the present description.
Figure 4B:
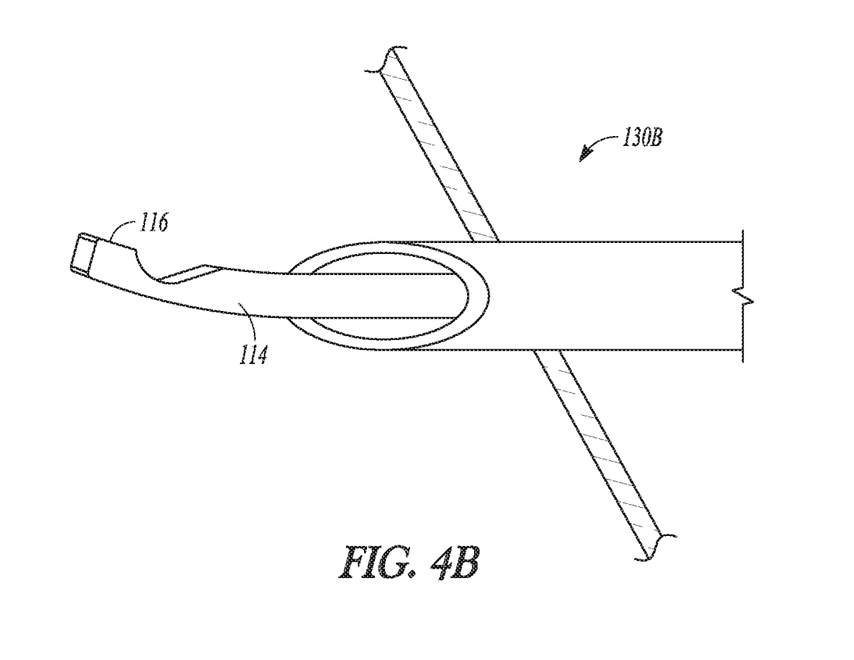
FIG. 4B provides a view of the hook of an exemplary suture capture device in a first rotatable position according to the present description.
Figure 5:
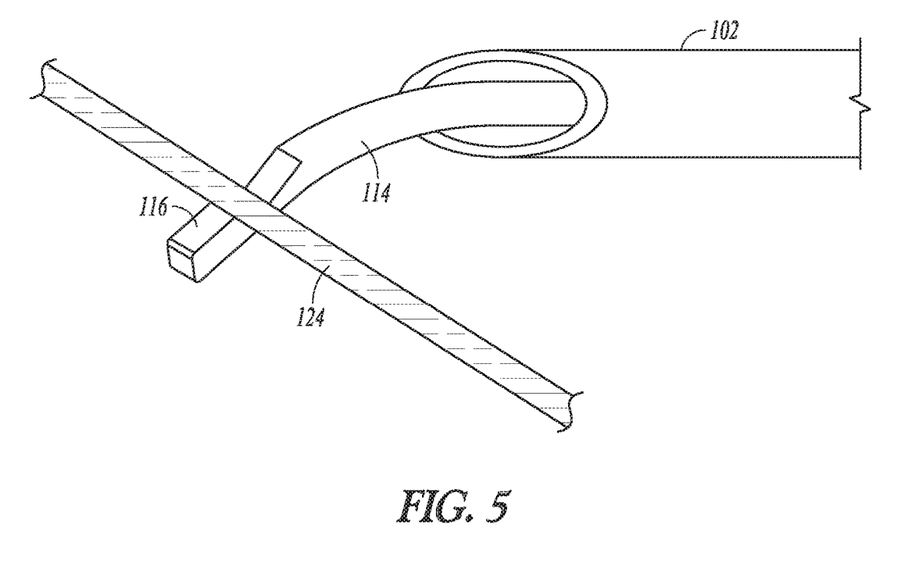
FIG. 5 provides a view of the hook of an exemplary suture capture device engaged with a suture according to the present description.

When the elongate hook member 114 is advanced out of the first end 104 of the elongate cannulated tool, the hook member 114 and hook 116 can be rotated by the operator of the device 100 until the hook 116 engages a suture 124. The combination of a curved elongate hook member 114 and ability to rotate the hook member enables a user to engage a suture even when the elongate cannulated tool 102 is not inserted immediately proximate the suture. An example of rotation between a first rotatable position 130A and a second rotatable position 130B of the elongate hook member 114 and associated hook 116 can be found by comparing FIGS. 4A and 4B. A suture capture device 100 in which the hook 116 has engaged a suture 124 is shown in FIG. 5. The suture 124 can, in various examples, be a #1 or #2 type suture.

Figure 6:
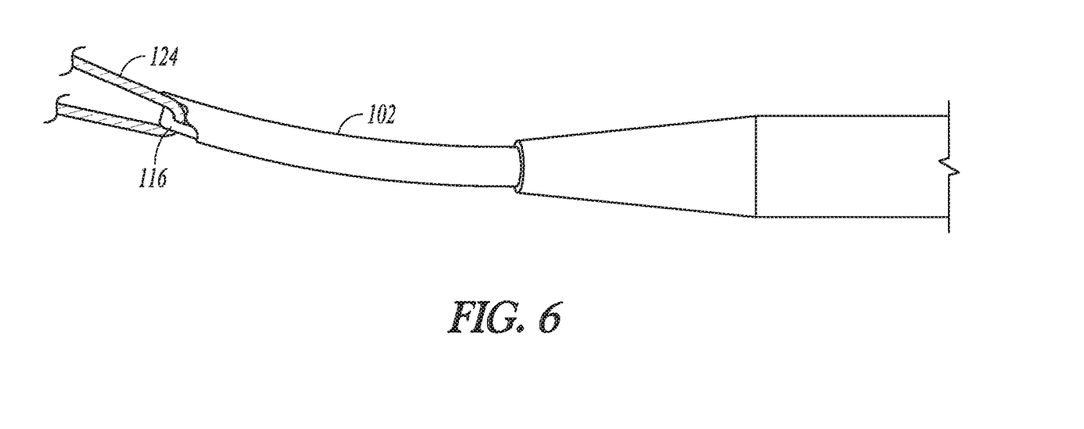
FIG. 6 provides a view of an exemplary suture capture device can suture in partially locked position according to the present description.
Figure 7A:
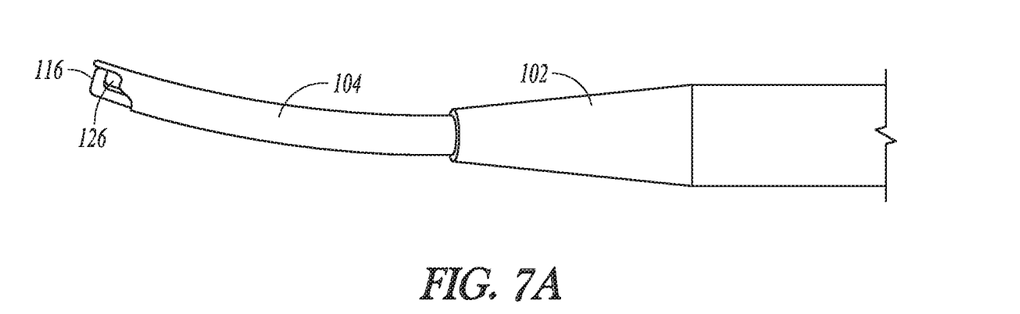
FIG. 7A provides a side view of an end of a suture capture device without a suture when in a partially locked position according to the present description.
Figure 7B:
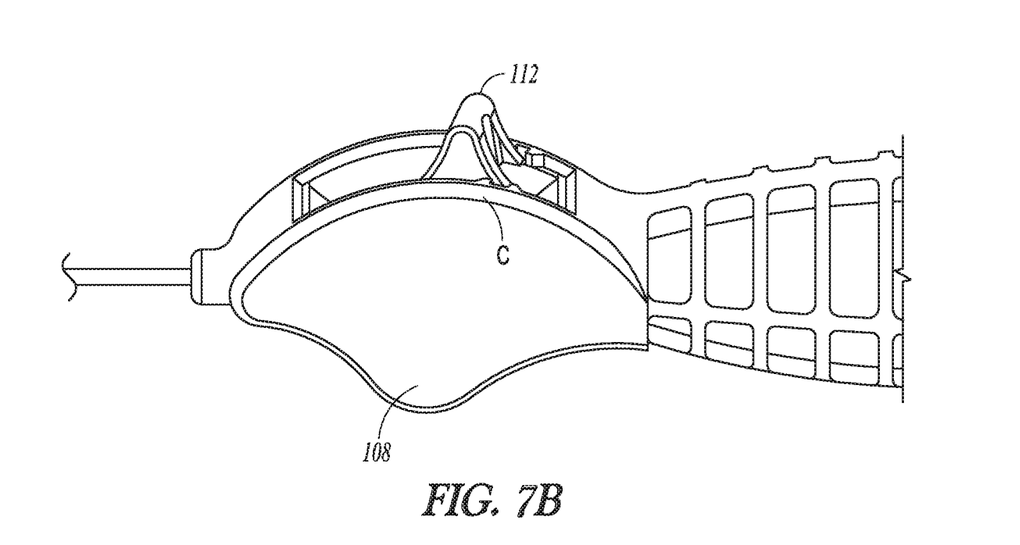
FIG. 7B provides a perspective view of a handle of an exemplary suture capture device in a partially locked configuration according to the present description.
Figure 8:
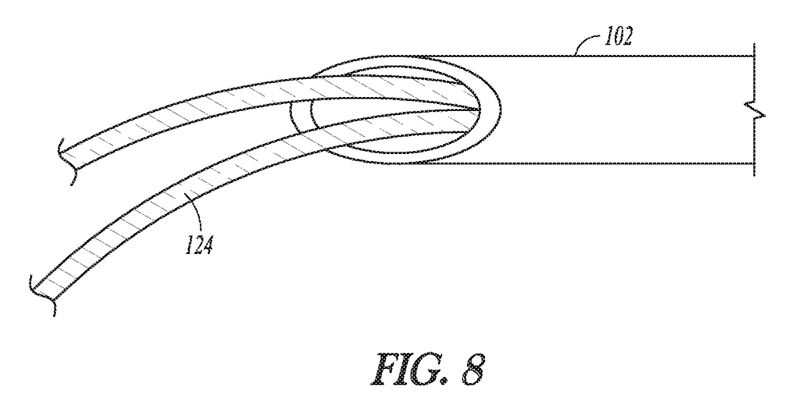
FIG. 8 provides a perspective view of an exemplary suture capture device and suture in a fully locked position according to the present description.

In one example, in order to "capture" the suture and lock it, at least partially, into place, the hook 116 can be retracted toward the elongate cannulated tool 102. For example, once the hook 116 has engaged a suture 124 and the suture is positioned within the hook 116 (as illustrated in FIG. 5) the elongate hook member 114 and hook 116 can be retracted (as shown in FIG. 6), until the suture 124 presses against the elongate cannulated tool 102. When in this "partially locked position", the suture 124 is capable of sliding relative to the hook (e.g., along a longitudinal axis of the suture) but not capable of escaping the hook 116 (or more specifically the eye or channel created by the hook 116 and tool 102). FIGS. 7A and 7B provide views of the first end 104 of the elongate cannulated tool 102 and the handle 108 and trigger 112, respectively, in this partially locked position. As shown, the hook 116 and first end 104 of elongate cannulated tool can create an eye 126 (or channel) in which the suture 124 is held but is allowed to slide relative to the hook. The operator may be able to determine that the device is in the partially locked position because the trigger 112 may "click" when it reaches position C, which corresponds to the partially locked trigger position. Where it is desirable to "fully lock" the suture (such that it is also incapable of sliding), the elongate hook member 114, hook 116 and suture 124 can all be fully retracted within the hollowed center region 134 of the elongate cannulated tool 102, as shown in FIG. 8 (with elongate hook member 114 hidden from view).

Figure 9A:
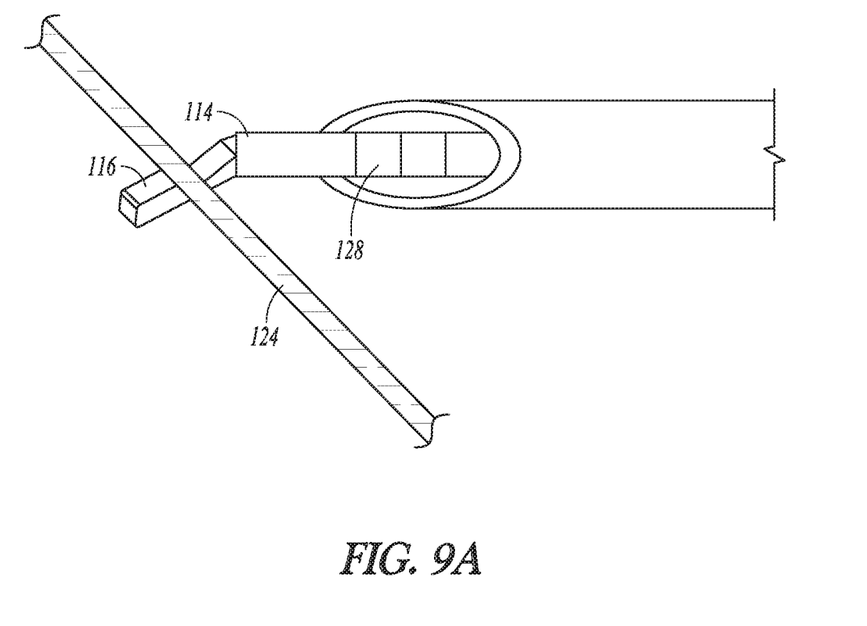
FIGS. 9A and 9B provide perspective views of a suture capture device that includes an elongate sleeve used to lock the suture in position according to the present description.
Figure 9B:
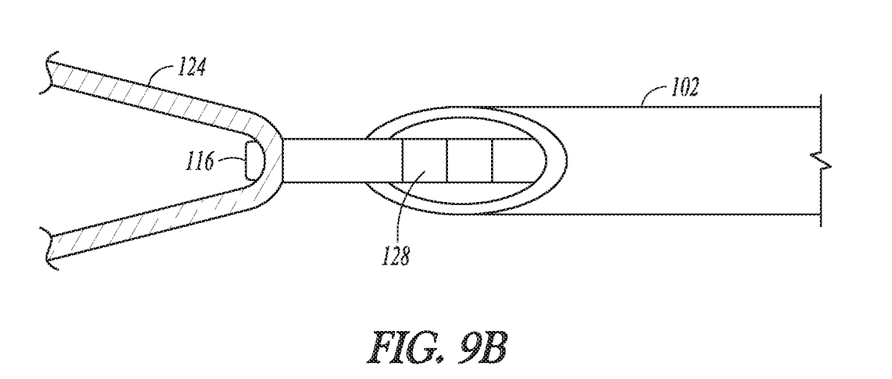

FIGS. 9A and 9B illustrate yet another exemplary aspect of a suture capture device according to the present description. In some examples, the suture capture device 100 can include an elongate sleeve 128. In one embodiment, the elongate sleeve can be metal, for example, a stainless steel sleeve. The elongate sleeve 128 can be positioned around at least a portion of the elongate hook member 114, but can also be positioned within the hollowed center region 134 of the elongate cannulated tool 102 such that the portion of the sleeve 128 within the hollowed center region 134 is positioned between the elongate hook member 114 and walls of the hollowed center region 134 of the elongate cannulated tool 102. The elongate sleeve 128 can be configured to be advanced (as shown in FIG. 9B) in order to clamp a suture 124 against a portion of the hook 116. When fully advanced, the compression on the suture 124 created by the elongate sleeve 128 and hook 116 can cause the suture to be "fully locked", i.e., incapable of escaping the hook 116 and incapable of sliding. Alternatively, the sleeve 128 may only be advanced so far as to partially lock the suture 124 in place (as described in the previous example).

In any of the example above, once a suture 124 has been placed in a fully locked or partially locked position with respect to the suture grasping device 100, the suture can be routed by the operator to a desired location. After the suture has been moved to its desired position, the suture can be disengaged from the hook by either advancing the elongate hook member 114 back out of the hollowed center region of the elongate cannulated tool 102 and turning the elongate hook member 114, or by retracting (where present) the elongate sleeve 128 away from the hook 116.

Figures 10A, 10B:
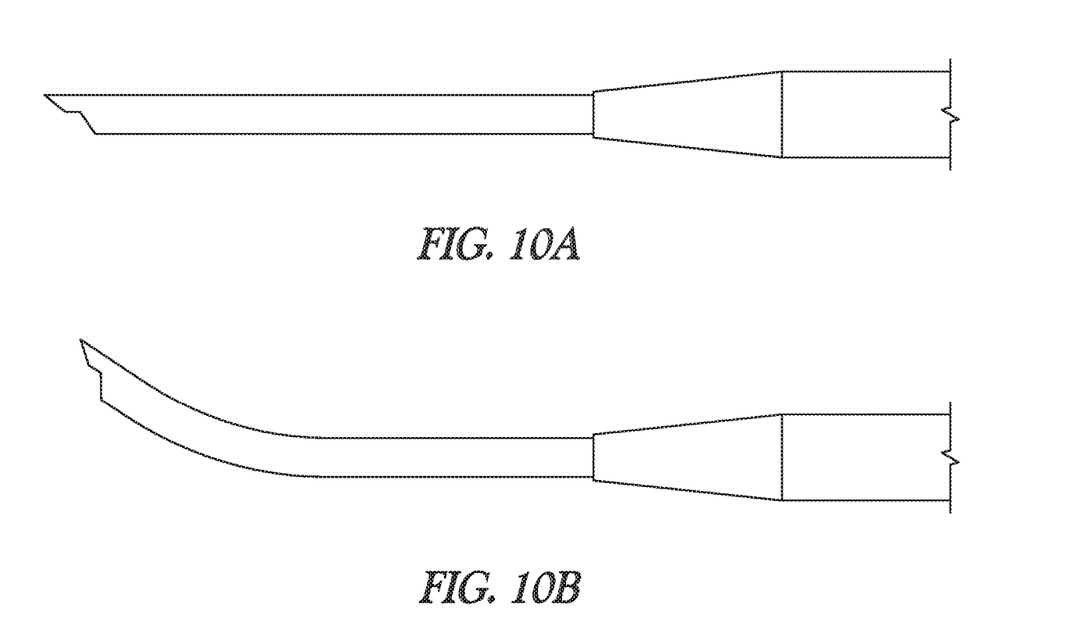
FIGS. 10A-10E provide side or perspective views of exemplary piercing ends of elongate cannulated tools according to the present description.
Figure 10C:
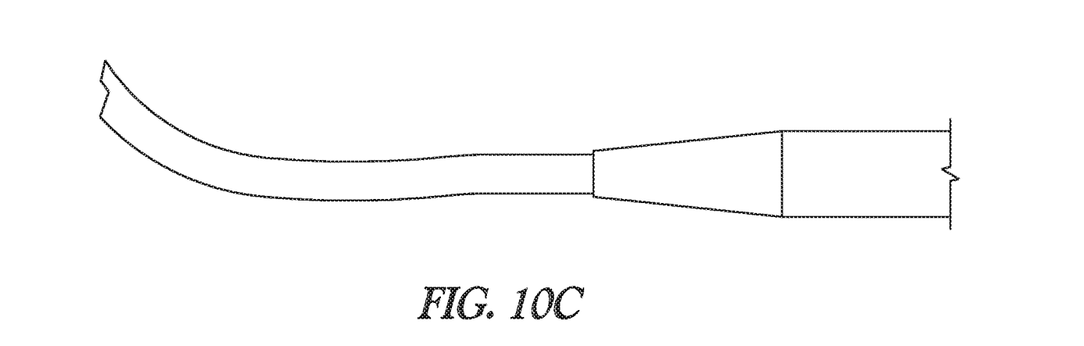
Figure 10D:
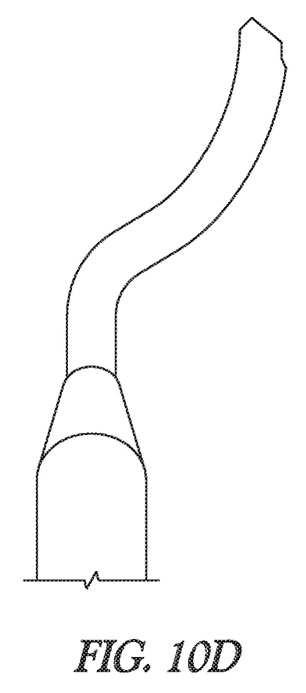
Figure 10E:
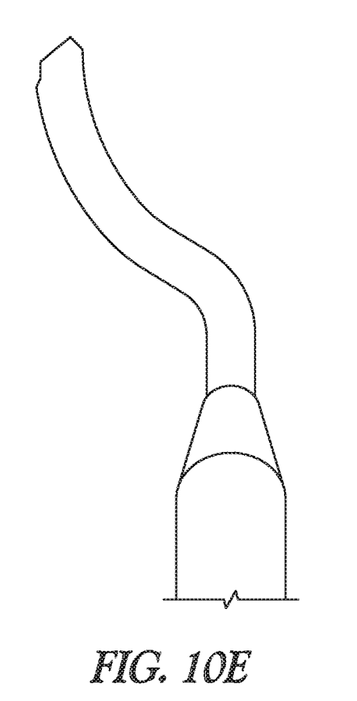

As shown in FIG. 1, the first end 104 of the elongated tool and sharpened point 106 can generally be straight, i.e., continuing along the direction of the longitudinal axis of the elongate cannulated tool 102. Such a construction is also illustrated in FIG. 10A. However, as shown in FIGS. 10B, 10C, 10D and 10E, the first end of the elongated tool according to the present description can, in some examples, be curved, such that the direction of the point 106 is not along the longitudinal axis of the majority of the elongate cannulated tool 102.

In another aspect, the present description relates to a method of capturing a suture. The method can include inserting a first end of an elongate cannulated tool 102 into an incision proximate a suture 124; advancing an elongate hook member 114 through a hollowed center region of the elongate cannulated tool 102, a hook 116 of the elongate hook member 114 advancing out a first end 104 of the elongate cannulated tool 102; engaging the hook 116 with the suture 124; locking the suture 124 into position with respect to the hook 116; and moving the suture 124 to a desired position by moving the elongate cannulated tool 102. The method can further include creating the incision using the sharpened point 106 on the first end 104 of the elongate cannulated tool 102.

Various Notes & Examples

In Example 1 a suture capture device can include: an elongate cannulated tool, a first end of the elongate cannulated tool comprising a sharpened point configured to pierce tissue; an elongate hook member positioned within a hollowed center region of the elongate cannulated tool, the elongate hook member comprising a hook on a first end of the elongate hook member that is positionable proximate the sharpened point of the elongate cannulated tool, the elongate hook member capable of advancing and retracting within the elongate cannulated tool; a handle positioned on a second end of the elongate cannulated tool opposite the first end, the handle comprising a trigger that advances the hook out of the first end of the elongate cannulated tool when moved in a first direction and retracts the hook into the hollowed portion of the elongate cannulated tool when moved in a second direction opposite the first direction.

In Example 2, the device of Example 1 can optionally be configured such that when a suture is positioned within the hook and the hook retracted until the suture presses against the elongate cannulated tool, the suture is capable of sliding relative to the hook.

In Example 3, the device of one or any combination of Examples 1-2 can optionally be configured to further include an elongate sleeve positioned around at least a portion of the elongate hook member, the elongate sleeve configured to be advanced in order to clamp a suture against a portion of the hook.

In Example 4, the device of Example 3 can optionally be configured such that elongate sleeve comprises stainless steel.

In Example 5, the device of one or any combination of Examples 1-4 can optionally be configured to further include that the hook includes a recess of sufficient depth to accommodate a #2 suture.

In Example 6, the device of one or any combination of Examples 1-5 can optionally be configured to further include that the elongate hook member is rotatable within the elongate cannulated tool.

In Example 7, the device of one or any combination of Examples 1-6 can optionally be configured to further include that a portion of the elongate hook member proximate the hook curves in a direction away from an axis of the sharpened point when the elongate hook member is advanced out the first end of the elongate cannulated tool.

In Example 8, the device of one or any combination of Examples 1-7 can optionally be configured to further include that when a suture is positioned within the hook and retracted until the suture is pulled at least partly within the elongate cannulated tool, the suture is incapable of sliding or escape from the hook.

In Example 9, the device of one or any combination of Examples 1-8 can optionally be configured to further include that the elongate cannulated tool comprises stainless steel.

In Example 10, the device of one or any combination of Examples 1-9 can optionally be configured to further include that the elongate hook member comprises nitinol.

In Example 11 a method of capturing a suture can include: inserting a first end of an elongate cannulated tool into an incision proximate a suture; advancing an elongate hook member through a hollowed center region of the elongate cannulated tool, a hook of the elongate hook member advancing out a first end of the elongate cannulated tool; engaging the hook with the suture; locking the suture into position with respect to the hook; and moving the suture to a desired position by moving the elongate cannulated tool.

In Example 12, the method of Example 11 can optionally further include that locking the suture comprises creating a channel through which the suture can slide relative to the hook but not escape the hook.

In Example 13, the method of one or any combination of Examples 11-12 can optionally further include that locking the suture comprises securing the suture such that it cannot escape the hook or slide relative to the hook.

In Example 14, the method of one or any combination of Examples 11-13 can optionally further include that locking the suture comprises retracting the hook to the entrance to the hollowed center region proximate the first end of the elongate cannulated tool such that the suture is placed in compression between the hook and the elongate cannulated tool.

In Example 15, the method of one or any combination of Examples 11-14 can optionally further include that locking the suture comprises advancing a sleeve positioned around the hook member and with the hollowed center region of the elongate cannulated tool until the sleeve contacts the suture and places the suture in compression between the sleeve and the hook.

In Example 16, the method of one or any combination of Examples 11-15 can optionally further include that engaging the hook with the suture comprises rotating the hook member until it contacts the suture.

In Example 17, the method of one or any combination of Examples 11-16 can optionally further include that the suture comprises a #1 or #2 suture.

In Example 18, the method of one or any combination of Examples 11-17 can optionally further include disengaging the hook from the suture after the suture has been moved to a desired position.

In Example 19, the method of one or any combination of Examples 11-18 can optionally further include creating the incision using a sharpened point on the first end of the elongate cannulated tool.

In Example 20, the method of one or any combination of Examples 11-19 can optionally include that a portion of the elongate hook member proximate the hook curves in a direction away from the longitudinal axis of elongate cannulated tool when the elongate hook member is advanced out the end of the elongate cannulated tool.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 172(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A suture capture device, comprising:
    an elongate cannulated tool, a first end of the elongate cannulated tool comprising a sharpened point configured to pierce tissue;
    an elongate hook member positioned within a hollowed center region of the elongate cannulated tool, the elongate hook member comprising a hook on a first end of the elongate hook member that forms a recess of sufficient depth to capture a suture, wherein the hook is positionable proximate the sharpened point of the elongate cannulated tool and can advance outward thereof, the elongate hook member capable of advancing and retracting within the elongate cannulated tool, wherein the elongate hook member includes a projection spaced longitudinally from the hook a distance from the first end; and
    a handle positioned on a second end of the elongate cannulated tool opposite the first end, the handle comprising a trigger that advances the hook out of the first end of the elongate cannulated tool when moved in a first direction and retracts the hook into the hollowed portion of the elongate cannulated tool when moved in a second direction opposite the first direction;
    wherein the device is configured with two locking positions, wherein in a first locking position of the two locking positions the suture is captured by the hook but is slidable relative to the hook, wherein in a second locking position of the two locking position the hook is retracted until the suture is captured between the hook and the elongate cannulated tool and the suture and non-slidable relative to the hook.

2. The suture capture device of claim 1, wherein the recess is of sufficient depth to accommodate a #2 suture.

3. The suture capture device of claim 1, wherein a portion of the elongate hook member proximate the hook curves in a direction away from an axis of the sharpened point when the elongate hook member is advanced out the first end of the elongate cannulated tool.

4. The suture capture device of claim 1, wherein the elongate cannulated tool comprises stainless steel.

5. The suture capture device of claim 1, wherein the elongate hook member comprises nitinol.

6. A suture capture device, comprising:
    an elongate cannulated tool, a first end of the elongate cannulated tool comprising a sharpened point configured to pierce tissue;
    an elongate hook member positioned within a hollowed center region of the elongate cannulated tool, the elongate hook member comprising a hook on a first end of the elongate hook member that forms a recess of sufficient depth to capture a suture, wherein the hook is positionable proximate the sharpened point of the elongate cannulated tool and can advance outward thereof, the elongate hook member capable of advancing and retracting within the elongate cannulated tool, wherein the elongate hook member includes a projection spaced longitudinally from the hook a distance from the first end; and
    a handle positioned on a second end of the elongate cannulated tool opposite the first end, the handle comprising a trigger that advances the hook out of the first end of the elongate cannulated tool when moved in a first direction and retracts the hook into the hollowed portion of the elongate cannulated tool when moved in a second direction opposite the first direction, wherein the elongate hook member is rotatable within the elongate cannulated tool to engage the suture.

\* \* \* \* \*